United States Patent [19]

Dierdorf et al.

[11] Patent Number: 5,705,680

[45] Date of Patent: Jan. 6, 1998

[54] PROCESS FOR THE PREPARATION OF O-ACYLGLYCOLANILIDES

[75] Inventors: Andreas Dierdorf; Theodor Papenfuhs, both of Frankfurt, Germany

[73] Assignee: Hoechst Aktiengesellschaft, Germany

[21] Appl. No.: 510,905

[22] Filed: Aug. 3, 1995

[30] Foreign Application Priority Data

Aug. 5, 1994 [DE] Germany ............... 44 27 837.3

[51] Int. Cl.$^6$ ............... C07C 67/02; C07C 69/76; C07C 255/00
[52] U.S. Cl. ............... 560/250; 560/106; 560/110; 558/392; 558/393; 558/414
[58] Field of Search ............... 560/106, 110, 560/250; 558/392, 393, 414

[56] References Cited

U.S. PATENT DOCUMENTS 4,509,971  4/1985  Förster et al. .

FOREIGN PATENT DOCUMENTS

| 0 005 501 | 5/1977 | European Pat. Off. . |
|---|---|---|
| 30 38 598 | 11/1993 | Germany . |
| 52-062234 | 9/1978 | Japan . |
| 50148321 | 5/1982 | Japan . |
| 93/22278 | 4/1979 | WIPO . |

OTHER PUBLICATIONS

European Search Report No. 95111896.7, Nov. 15, 1995.

*Primary Examiner*—Paul F. Shaver
*Attorney, Agent, or Firm*—Connolly & Hutz

[57] ABSTRACT

The present invention relates to a process for the preparation of O-acylglycolanilides of the formula (1)

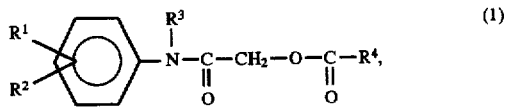

in which $R^1$ and $R^2$ are identical or different and are hydrogen, halogen, a nitro group, a cyano group, a straight-chain or branched alkyl, alkenyl, alkynyl or alkoxy group having from 1 to 12 carbon atoms, an aralkyl group having from 7 to 12 carbon atoms, a cycloalkyl group having from 6 to 12 carbon atoms or an aryl group having from 6 to 12 carbon atoms,. $R^3$ is hydrogen or a straight-chain or branched alkyl group having from 1 to 12 carbon atoms, and $R^4$ is an alkyl group having from 1 to 6 carbon atoms or is a substituted or unsubstituted phenyl radical, in which an aniline of the formula (2)

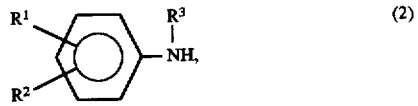

in which $R^1$, $R^2$ and $R^3$ have the same meaning as in formula (1), and an O-acylglycolic acid of the general formula (3)

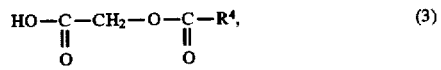

in which $R^4$ has the same meaning as in formula (1), are reacted with an inorganic acid halide, optionally in the presence of an inert organic solvent, at from 20° to 180° C.

16 Claims, No Drawings

PROCESS FOR THE PREPARATION OF O-ACYLGLYCOLANILIDES

The present invention relates to a process for the preparation of O-acylglycolanilides which is superior to the state of the art.

O-Acylglycolanilides, in particular acetoxyacetanilides, represent promising precursors for preparing glycol anilides. Glycolanilides, in turn, are important starting compounds both for preparing herbicides (EP-A-300 344) and pharmaceutical active compounds (EP-A-284 338 and EP-A-363 284) and also for preparing fungicides (U.S. Pat. No. 4 440 780).

Owing to the importance of this group of substances, there has been no lack of attempts in the past to prepare hydroxy carboxamides and, in particular, hydroxy carboxanilides, for example glycolanilides, by different routes.

For example, DE-A-30 38 598 discloses a process for preparing α-hydroxycarboxamides by reacting α-acyloxycarboxamides (O-acylated α-hydroxycarboxamides), in particular α-formyloxycarboxamides, with alkyl alcohols in the presence of catalytic quantities of alkali metal or alkaline earth metal hydroxides, hydrogen carbonates or carbonates. The corresponding α-acyloxycarboxamides are obtained by reacting α-chlorocarboxamides with alkali metal formates or acetates. Since the α-chlorocarboxamides which are required for this reaction have to be prepared in a separate step, for example by reacting an amine with the corresponding α-chlorocarbonyl chloride, preparation of the α-oxycarboxamides is in reality a two-step process which, in addition, also suffers from the disadvantage that the α-oxycarboxamides are prepared in the presence of a quaternary ammonium salt. It is, however, known that quaternary ammonium salts of this nature give rise to problems in waste water purification.

DE-A-29 04 490 discloses another process for preparing α-hydroxycarboxamides by transesterifying acetoxycarboxamides with alcohols in the presence of catalytic quantities of an alkali metal or alkaline earth metal hydroxide or alkali metal or alkaline earth metal carbonate. The corresponding α-halocarboxamides are reacted with an alkali metal or alkaline earth metal acetate, in the presence of a quaternary ammonium salt and, where appropriate, using a diluent, to form the corresponding α-acetoxycarboxamides.

Since the α-chlorocarboxamides which are required for this purpose have to be prepared in a separate step, for example by reacting an amine with the corresponding chlorocarbonyl chloride, the preparation of the α-acetoxycarboxamides is likewise a two-step process in which the use of quaternary ammonium salts likewise results in undesirable pollution of the waste water.

U.S. Pat. No. 4 509 971 describes, in column 6, line 41 to column 7, line 16, and column 26, lines 14 to 56, a process for preparing acetoxyacetamides and, in particular, acetoxyacetanilides, which proceeds from hydroxyacetic acid. Hydroxyacetic acid is first reacted, in a separate step, with acetyl chloride, resulting in acetoxyacetic acid. In a subsequent step, the acetoxyacetic acid is reacted directly with thionyl chloride to form acetoxyacetyl chloride, which is then isolated. The corresponding acetoxyacetamides or acetoxyacetanilides are obtained by reacting the acetoxyacetyl chloride with a secondary amine or aniline.

Therefore, when acetoxyacetic acid is used as the starting material, two steps are required for preparing the corresponding acetoxyacetamides or acetoxyacetanilides, that is, firstly, reaction of acetoxyacetic acid with thionyl chloride and isolation of the acetoxyacetyl chloride and, secondly, reaction of the acetoxyacetyl chloride with the secondary amine or aniline.

The processes described above are relatively elaborate, since they involve the preparation of the desired α-acetoxyacetamides (O-acetylglycolamides) by way of two separate, consecutive reaction steps. In addition, the quaternary ammonium salts which are used as phase transfer catalysts give rise to problems with the waste products which arise during the course of the reaction. They are particularly undesirable due to their unfavourable properties in the waste water.

In view of the importance of O-acylglycolanilides as precursors for preparing glycolanilides, there is interest in the object of making available a process for preparing O-acylglycolanilides which, on the one hand, avoids the disadvantages of the abovementioned processes and, on the other, is easy to implement and uses readily available starting materials and, in addition, provides the desired O-acylglycolanilides in good yield and in a high degree of purity.

This object is achieved by a process for the preparation of O-acylglycolanilides of the formula (1)

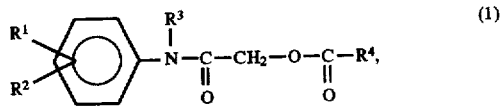

in which $R^1$ and $R^2$ are identical or different and are hydrogen, halogen, a nitro group, a cyano group, a straight-chain or branched alkyl, alkenyl, alkynyl or alkoxy group having from 1 to 12 carbon atoms, an aralkyl group having from 7 to 12 carbon atoms, a cycloalkyl group having from 6 to 12 carbon atoms or an aryl group having from 6 to 12 carbon atoms, $R^3$ is hydrogen or a straight-chain or branched alkyl group having from 1 to 12 carbon atoms, and $R^4$ is an alkyl group having from 1 to 6 carbon atoms or is a substituted or unsubstituted phenyl radical. In this process, an aniline of the formula (2)

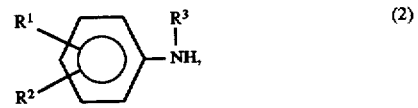

in which $R^1$, $R^2$ and $R^3$ have the same meaning as in formula (1), and an 0-acylglycolic acid of the formula (3)

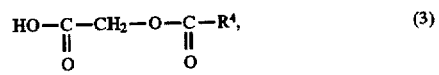

in which $R^4$ has the same meaning as in formula (1), are reacted with an inorganic acid halide, optionally in the presence of an inert organic solvent, at from 20° to 180° C.

The novel process exhibits several advantages. In the first place, it leads—as the following reaction equation, using $PCl_3$ as the inorganic acid halide illustrates by way of example—to the desired O-acylglycolanilides in a single reaction step.

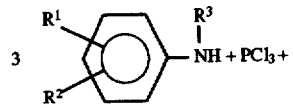

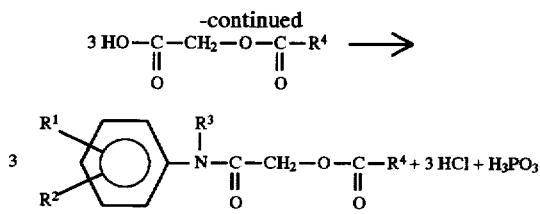

As can be seen from the reaction equation, the aniline of the formula (2), the O-acylglycolic acid of the formula (3) and the inorganic acid chloride react simultaneously with each other, and the desired O-acylglycolanilides of the formula (1) are formed directly.

In the second place, there is no need, therefore, for an elaborate isolation of any intermediate which is then subjected to further processing. In the third place, the use of quaternary ammonium salts as phase transfer catalysts can generally be dispensed with. In addition to this, the novel process can be effected in a technically unelaborate manner and using readily available starting compounds. The desired O-acylglycolanilides are obtained in good yield and, at the same time, at very high purity.

Once the reaction is complete, the inert organic solvent which may have been employed in the reaction can be separated off by distillation and can, if desired, be used once again for the reaction.

As is evident from the above discussion, a relatively large number of different anilines can be reacted in the novel process. In particular, anilines of the formula (2) can be employed in which $R^1$ and $R^2$ are identical or different and are hydrogen, halogen, a nitro group, a straight-chain or branched alkyl or alkoxy group having from 1 to 4 carbon atoms, or an aralkyl group having from 7 to 12 carbon atoms, in particular are hydrogen, fluorine, chlorine, bromine, or an alkyl or alkoxy group having from 1 to 4 carbon atoms, and preferably are hydrogen, fluorine, chlorine, bromine, or an alkyl group having from 1 to 4 carbon atoms.

As already mentioned at the outset, an aniline of the formula (2) is employed in which $R^3$ is hydrogen or a straight-chain or branched alkyl group having from 1 to 12 carbon atoms, in particular an aniline of the formula (2) in which $R^3$ is hydrogen or a straight-chain or branched alkyl group having from 1 to 4 carbon atoms, preferably an aniline of the formula (2) in which $R^3$ is an isopropyl group.

Examples of some suitable anilines are, without making any claim to be exhaustive, 2-methoxyaniline, 4-methoxyaniline, 3,5-dimethylaniline, 2-chloroaniline, 4-chloroaniline, N-methylaniline, N-ethylaniline, N-isopropylaniline and N-isopropyl-4-fluoroaniline.

An O-acylglycolic acid of the formula (3) is employed in the reaction in which $R^4$ is an alkyl group having from 1 to 6 carbon atoms or an optionally substituted phenyl radical, in particular is an alkyl group having from 1 to 4 carbon atoms, for example is a methyl, ethyl, n-propyl or i-propyl group, or a phenyl radical, and preferably is a methyl group.

Examples of O-acylglycolic acids are acetoxyacetic acid, O-propionylglycolic acid, O-n-butyrylglycolic acid, O-isobutyrylglycolic acid and O-n-valerylglycolic acid.

An inorganic acid chloride or acid bromide is used as the inorganic acid halide. Examples of suitable inorganic acid halides are phosphorus trichloride, phosphorus pentachloride, thionyl chloride or phosphorus tribromide, in particular phosphorus trichloride or thionyl chloride, preferably phosphorus trichloride.

The reaction may be carried out in the absence or presence of a solvent. The solvent which is used should be inert under the conditions of the reaction. Examples of suitable inert organic solvents are benzene, toluene, o-xylene, m-xylene, p-xylene, a mixture of isomeric xylenes, chlorobenzene, dichlorobenzene, chlorotoluene or diethyl ether, in particular toluene, o-xylene, m-xylene, p-xylene or a mixture of isomeric xylenes.

As already explained, the reaction is normally carried out at from 20° to 180° C. In many cases, it has proved to be of value to allow the reaction to proceed at from 60 to 160° C., in particular at from 90° to 150° C.

No particular demands are placed on the order in which the three reactants, namely the aniline of the formula (2), the o-acylglycolic acid of the formula (3) and the inorganic acid halide, are added to the reaction. The reactants can be supplied to the reaction in any order whatever.

The process becomes particularly simple if the aniline of the formula (2) and the O-acylglycolic acid of the formula (3), where appropriate together with an inert organic solvent, are introduced initially and the inorganic acid halide, where appropriate together with an inert organic solvent, is then metered in. Naturally, it is necessary, in a general manner, to ensure that the reactants are thoroughly mixed.

In general, the aniline of the formula (2), the acyloxyacetic acid of the formula (3) and the inorganic acid halide are employed in a molar ratio, or in a ratio of their equivalents, of 1:(0.5 to 1.5):(0.2 to 3), in particular 1:(0.75 to 1.25):(0.5 to 2), preferably 1:(0.9 to 1.1):(0.8 to 1.3).

The novel process can be carried out under reduced pressure, under atmospheric pressure or under elevated pressure. It may be particularly simply carried out under atmospheric pressure. In some cases, it may be advantageous to allow the reaction to proceed under elevated pressure, for example under the reaction pressure which is generated in a particular case. The process can be carried out continuously or discontinuously. It is found to be particular simple to carry out the process discontinuously.

The following examples illustrate the invention without limiting it.

EXPERIMENTAL SECTION

EXAMPLE 1

Preparation of acetoxyacetic acid N-isopropyl(4-fluoroanilide)

11.8 g (0.1 mol) of acetoxyacetic acid and 16.8 g (0.11 mol) of 4-fluoro-N-isopropylaniline in 100 ml of toluene are initially introduced into a reaction flask. A solution of 5.1 g (0.037 mol) of phosphorus trichloride in 30 ml of toluene is added dropwise at room temperature and while stirring. The contents of the flask are then boiled under reflux. While this is being done, the course of the reaction is monitored by gas chromatography. After 4 hours, the mixture is allowed to cool down to room temperature, and a solution of 3 g (0.022 mol) of phosphorus trichloride in 10 ml of toluene is added dropwise. The reaction mixture is boiled once again under reflux for 8 hours. The toluene phase is extracted by shaking with water and the solvent is removed in vacuo. The residue is crystallized by treating with petroleumether. 16.5 g (65.1% of theory) of acetoxyacetic acid N-isopropyl(4-fluoroanilide) are obtained with a purity of 98.8% (SC).

EXAMPLE 2

Preparation of acetoxyacetic acid N-isopropyl(4-fluoroanilide)

23.6 g (0.2 mol) of acetoxyacetic acid and 30.6 g (0.2 mol) of 4-fluoro-N-isopropylaniline in 200 ml of toluene are initially introduced into a reaction flask. A solution of 26.2 g (0.22 mol) of thionyl chloride in 40 ml of toluene is added dropwise at room temperature and while stirring. The contents of the flask are then heated to 100°–110° C. The course of the reaction is monitored by gas chromatography. After 2 hours, the reaction mixture is allowed to cool down to room temperature and is washed with water. The solvent is then distilled off in vacuo and the residue is crystallized by being treated with petroleum ether. 37.3 g (73.7% of theory) of acetoxyacetic acid N-isopropyl(4-fluoroanilide) are obtained with a purity of 98.5% (GC).

EXAMPLE 3

Preparation of 2-methoxy(α-acetoxyacetic acid) anilide 23.6 g (0.2 mol) of acetoxyacetic acid and 24.6 g (0.2 mol) o-anisidine in 200 ml of toluene are initially introduced into a reaction flask. A solution of 26.2 g (0.22 mol) of thionyl chloride in 40 ml of toluene is added dropwise at room temperature and while stirring. The contents of the flask are then heated to 100°–110° C. The course of the reaction is monitored by gas chromatography. After 1 hour, the reaction mixture is allowed to cool down to room temperature and is washed with water. The solvent is then distilled off in vacuo and the residue is crystallized by being treated with petroleum ether. 29.8 g (62.6% of theory) of 2-methoxy(α-acetoxyacetic acid)anilide are obtained with a purity of 91.4% (GC).

We claim:

1. A process for the preparation of O-acylglycol-anilides of the formula (1)

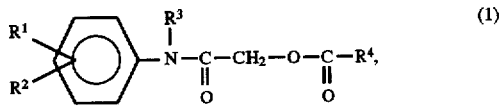

in which $R^1$ and $R^2$ are identical or different and are hydrogen, halogen, a nitro group, a cyano group, a straight-chain or branched alkyl, alkenyl, alkynyl or alkoxy group having from 1 to 12 carbon atoms, an aralkyl group having from 7 to 12 carbon atoms, a cycloalkyl group having from 6 to 12 carbon atoms or an aryl group having from 6 to 12 carbon atoms, $R^3$ is hydrogen or a straight-chain or branched alkyl group having from 1 to 12 carbon atoms, and $R^4$ is an alkyl group having from 1 to 6 carbon atoms or is a substituted or unsubstituted phenyl radical, which comprises reacting an aniline of the formula (2)

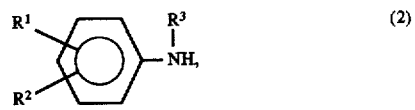

in which $R^1$, $R^2$ and $R^3$ have the same meaning as in formula (1), and an O-acylglycolic acid of the formula (3)

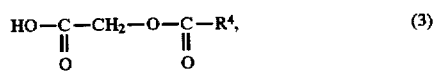

in which $R^4$ has the same meaning as in formula (1), with an inorganic acid halide, and optionally in the presence of an inert organic solvent, at from 20° to 180° C.

2. The process as claimed in claim 1, wherein an aniline of the formula (2) is employed in which $R^1$ and $R^2$ are identical or different and are hydrogen, halogen, a nitro group, a straight-chain or branched alkyl or alkoxy group having from 1 to 4 carbon atoms, or an aralkyl group having from 7 to 12 carbon atoms.

3. The process as claimed in claim 1, wherein an aniline of the formula (2) is employed in which $R^1$ and $R^2$ are identical or different and are hydrogen, fluorine, chlorine, bromine, or an alkyl or alkoxy group having from 1 to 4 carbon atoms.

4. The process as claimed in claim 1, wherein an aniline of the formula (2) is employed in which $R^1$ and $R^2$ are identical or different and are hydrogen, fluorine, chlorine, bromine or an alkyl group having from 1 to 4 carbon atoms.

5. The process as claimed in claim 1, wherein an aniline of the formula (2) is employed in which $R^3$ is hydrogen or a straight-chain or branched alkyl group having from 1 to 4 carbon atoms.

6. The process as claimed in claim 1, wherein an aniline of the formula (2) is employed in which $R^3$ is an isopropyl group.

7. The process as claimed in claim 1, wherein an O-acylglycolic acid of the formula (3) is employed in which $R^4$ is a methyl, ethyl, n-propyl or i-propyl group or a phenyl radical.

8. The process as claimed in claim 1, wherein an O-acylglycolic acid of the formula (3) is employed in which $R^4$ is a methyl group.

9. The process as claimed in claim 1, wherein an inorganic acid chloride or acid bromide is employed as the inorganic acid halide.

10. The process as claimed in claim 1, wherein phosphorus trichloride, phosphorus pentachloride, thionyl chloride or phosphorus tribromide is employed as the inorganic acid halide.

11. The process as claimed in claim 1, wherein phosphorus trichloride or thionylchloride is employed as the inorganic acid halide.

12. The process as claimed in claim 1, wherein benzene, toluene, o-xylene, m-xylene, p-xylene, a mixture of isomeric xylenes, chlorobenzene, dichlorobenzene, chlorotoluene or diethyl ether is employed as the inert organic solvent.

13. The process as claimed in claim 1, wherein toluene, o-xylene, m-xylene, p-xylene or a mixture of isomeric xylenes is employed as the inert organic solvent.

14. The process as claimed in claim 1, wherein the reaction is carried out at from 60° to 160° C.

15. The process as claimed in claim 1, wherein the reaction is carried out at from 90° to 150° C.

16. The process as claimed in claim 1, wherein the aniline of the formula (2), the O-acylglycolic acid of the formula (3) and the inorganic acid halide are employed in a molar ratio of 1:(0.5 to 1.5):(0.2 to 3).

* * * * *